(12) United States Patent
Krahbichler et al.

(10) Patent No.: US 6,422,073 B1
(45) Date of Patent: Jul. 23, 2002

(54) DEVICE FOR IDENTIFYING LIQUID ANAESTHETICS

(75) Inventors: Erik Krahbichler, Pentling-Matting (DE); Tom Pessala, Bromma (SE)

(73) Assignee: Siemens Elema AB, Solna (SE)

( * ) Notice: Subject to any disclaimer, the term of this patent is extended or adjusted under 35 U.S.C. 154(b) by 568 days.

(21) Appl. No.: 08/900,720

(22) Filed: Jul. 28, 1997

(30) Foreign Application Priority Data

Aug. 9, 1996 (SE) ................................................ 9602960

(51) Int. Cl.[7] .......................... G01F 23/00; A61M 15/00; G01N 21/44; G01N 15/06
(52) U.S. Cl. ..................... 73/293; 128/203.15; 356/133; 250/573
(58) Field of Search ..................... 128/203.15; 250/573, 250/227.11; 356/133; 385/12; 73/293

(56) References Cited

U.S. PATENT DOCUMENTS

| | | | | |
|---|---|---|---|---|
| 3,282,149 A | * | 11/1966 | Shaw et al. ............... | 356/130 |
| 4,045,668 A | * | 8/1977 | Pitt et al. ................ | 250/227.25 |
| 4,187,025 A | | 2/1980 | Harmer | |
| 4,240,747 A | * | 12/1980 | Harmer ..................... | 356/133 |
| 4,433,913 A | | 2/1984 | Harmer | |
| 4,444,182 A | * | 4/1984 | Gregory ................ | 128/204.14 |
| 4,564,292 A | * | 1/1986 | Omet .......................... | 356/133 |
| 4,641,025 A | * | 2/1987 | Miller ................... | 250/227.11 |
| 4,690,562 A | * | 9/1987 | Davies et al. .............. | 356/361 |
| 4,834,533 A | | 5/1989 | Horike et al. | |
| 4,870,292 A | | 9/1989 | Alpert et al. | |
| 4,981,338 A | * | 1/1991 | Bobb et al. .................. | 385/12 |
| 4,998,022 A | * | 3/1991 | Chang et al. .............. | 250/577 |
| 5,231,591 A | * | 7/1993 | Flewelling et al. .......... | 702/24 |
| 5,272,907 A | | 12/1993 | Hakala | |
| 5,396,325 A | | 3/1995 | Carome et al. | |
| 5,730,119 A | * | 3/1998 | Lekholm ............... | 128/200.24 |

FOREIGN PATENT DOCUMENTS

| DE | 34 00 717 | 7/1984 |
|---|---|---|
| EP | 0 089 098 | 9/1983 |
| EP | 0 483 725 | 5/1992 |

* cited by examiner

*Primary Examiner*—Hezron Williams
*Assistant Examiner*—Jay L. Politzer
(74) *Attorney, Agent, or Firm*—Schiff Hardin & Waite (57) ABSTRACT

A device for use in an anaesthetic administration apparatus for identifying at least one liquid anaesthetic in the anaesthetic apparatus has a measuring unit for determining at least one parameter related to the refractive index of the liquid anaesthetic, a unit for determining the temperature of the liquid anaesthetic and an analysis unit for identifying the anaesthetic from the determined parameter.

17 Claims, 7 Drawing Sheets

DEVICE FOR IDENTIFYING LIQUID ANAESTHETICS

BACKGROUND OF THE INVENTION

1. Field of the Invention

The present invention relates to a device, intended for use in an anaesthetic administration apparatus, for identifying at least one liquid anaesthetic in the anaesthetic administration apparatus.

2. Description of the Prior Art

In general, narcosis or anaesthesia involves inducing a patient into a dormant state in which he or she is incapable of feeling any pain. The patient is usually administered a mixture of oxygen, nitrous oxide, an anaesthetic agent and (possibly) air from a respiratory circuit in an anaesthetic apparatus. The most common anaesthetic agents are halothane, desflurane, enflurane, isoflurane and sevoflurane. The anaesthetic agent is normally in liquid form in an anaesthetic vaporizer attached to the anaesthetic apparatus, and a desired amount of liquid anaesthetic is vaporized and sent to the respiratory circuit during anaesthesia.

The effect of different anaesthetic agents on the patient, which are administered to the patient in varying concentrations, varies. The side-effects of the different anaesthetic agents also vary. An anaesthetic apparatus is available which can be equipped with a number of anaesthetic vaporizers so as to give the anaesthesiologist a direct option of selecting the anaesthetic agent he or she deems best for the patient, with no need to mount or detach different anaesthetic vaporizers. In addition, the anaesthesiologist is able to switch to a different anaesthetic agent during ongoing surgery. This occurs in operations on e.g. infants or in protracted surgery.

The patient should never be given a mixture of different anaesthetic agents, since the effect of the mixture is hard to predict and largely unknown. That is why anaesthetic apparatuses are normally devised so they are only able to administer one anaesthetic agent at a time to the patient. The possibility of mixing a number of anaesthetic gases, however, is still a risk, even with an anaesthetic apparatus with only one anaesthetic vaporizer, viz. if different anaesthetic agents became intermixed when replenished anaesthetic agent is added to the active anaesthetic vaporizer.

To minimize the risk of errors in inducing anaesthesia, it would be advantageous if the anaesthetic system could automatically identify the anaesthetic agent administered to the patient. The anaesthetic apparatus then could be devised to issue an alarm if an error occurred.

As noted above, the various known anaesthetic agents are administered to the patient in different concentrations. If an erroneous concentration is set for a particular anaesthetic agent, the patient could be subjected to needless risk, entailing both overdosing and underdosing of the anaesthetic agent. An erroneous concentration will therefore most likely occur when the wrong anaesthetic agent is administered, since different concentrations are used for the different anaesthetic agents.

Even these risks would be greatly reduced if the anaesthetic agent could be identified before it is supplied to the patient.

In the anaesthesia field, identification of anaesthetic agents by optical methods, i.e. by absorption spectrophotometry, is known. Since a number of anaesthetic agents have similar absorption spectra, absorption must be measured at a number of wavelengths to permit reliable identification of a specific anaesthetic agent. This makes it necessary to use extensive measurement equipment for identifying an anaesthetic agent. Optical measurement is generally performed on the gas mixture supplied to the patient, i.e. the anaesthetic agent is present in gaseous form.

Another known way of identifying anaesthetics in gaseous form to employ two different measurement methods for determining the concentration of the anaesthetic agent, and to combine the results of these two methods to identify the anaesthetic agent. For example, an optical method, in which measurement of absorption is made at a specific wavelength for the anaesthetic agent, and a method using an oscillating crystal, coated with a layer of oil or grease which adsorbs and desorbs anaesthetic gas molecules, can be used. The crystal's oscillation frequency changes to varying degrees depending on the molecular weight and concentration of the anaesthetic gas. When a combination of these two measurement methods is employed, a unique signal is obtained for every known anaesthetic agent. It should be noted that measurement of changes in the oscillation frequency of a crystal is not in itself sufficient to permit identification of anaesthetic agents, since the frequency change is relatively the same for the different anaesthetic agents in the concentrations at which they are normally used. One such device is described in U.S. Pat. No. 5,272,907.

SUMMARY OF THE INVENTION

An object of the present invention is to provide a device, intended for use in an anaesthetic apparatus, for reliably and simply identifying at least one liquid anaesthetic in the anaesthetic apparatus. The device according to the present invention has a measuring unit for determining at least one parameter related to the refractive index of the liquid anaesthetic and a unit for determining the temperature of the liquid anaesthetic. The device further has an analysis unit for identifying the anaesthetic agent from the determined parameter.

One advantage of the device according to the present invention is that the analysis unit is able to determine, from the established parameters, whether a mixture of at least two anaesthetic agents is present. This further enhances patient safety in anaesthesia. Preferably, the analysis unit also identifies the liquid anaesthetics that have been mixed and the concentration of each liquid anaesthetic.

A first possibility to obtain the aforementioned parameter in accordance with the invention is to employ a light-emitter arranged so a light beam emitted thereby strikes the surface of the liquid anaesthetic at a specific angle of incidence. The device according to the present invention also has a position detector which is arranged to indicate any deflection of the light beam in the liquid. This deflection constitutes the parameter and depends on the liquid anaesthetic's refractive index and level.

The level can be standardized (maintained constant) by selecting the appropriate arrangement, e.g., by using a small container which receives a precise amount of liquid from the vaporizer. Such a test can be made at the onset of use of the anaesthetic apparatus and each time the vaporizer is filled with liquid anaesthetic. When the level is constant, the identity of the liquid anaesthetic can be determined based on temperature and deflection (refractive index).

In conjunction herewith, it is advantageous to arrange a measuring rod on the position detector to indicate the identity of the anaesthetic agent when the light beam strikes the position detector. If the light beam shines between two different "identity" positions, this means there is a mixture of different anaesthetics.

A second possibility to obtain the aforementioned parameter is for the measuring unit also to have an optical fiber which has one end adjacent the light-emitter means and another end arranged adjacent a photosensitive cell and a curved section immersed in the liquid anaesthetic. The measuring unit determines the amount of light which leaks out of the curved section of the optical fiber as the parameter.

Although similar devices are known (see e.g., U.S. Pat. No. 4,187,025) for determining refractive index or temperature of a known liquid, or discrete levels of a liquid in a container, they have not been utilized, nor suggested for use in determining the identity of anaesthetics in anaesthetic machines.

According to an embodiment of the invention, the part of the optical fiber immersed in the liquid anaesthetic has straight sections in addition to the curved section. In particular, the straight sections pass through the surface of the liquid anaesthetic at a right angle. This results in minimum light loss from the fiber is obtained as it passes from one surrounding refractive index (e.g., air) to another (the liquid anaesthetic).

The measuring unit can also have a second optical fiber, not immersed in the liquid anaesthetic, of the same length as the first fiber. This second fiber is intended to supply a reference value.

In a second embodiment of the invention, the measuring unit also has n similar optical fibers arranged at different levels in the liquid in order to determine the level of the liquid in discrete steps.

At least one of these optical fibers has a number of curved sections at different levels in the liquid in order to determine the level of the liquid.

The analysis unit can issue an alarm when the level of the liquid drops below the curved section of the fiber.

In a third embodiment simultaneous level measurements are made with the parameter determination in accordance with the invention wherein the device also has two electrodes for contacting any liquid anaesthetic which is present and for measuring the capacitance of the liquid between the electrodes. Since the liquid's capacitance varies with the level of the liquid, measuring this capacitance constitutes a level measurement.

In a first version of this third embodiment, the immersed part of the optical fiber has two substantially parallel sections, and the two electrode means are arranged along these parallel sections.

The two electrodes can be formed by respective metallized surface areas on the parallel sections of the optical fiber.

Alternatively the two electrodes can be formed by metal wire wound around the respective parallel sections of the optical fiber.

In a second version of the third embodiment, a first of the electrodes is formed by a metallized surface area on the optical fiber, and a second of the electrodes is formed by a metallic deposit on the inside of a container for the liquid anaesthetic.

DESCRIPTION OF THE PREFERRED EMBODIMENTS

Figure 1:
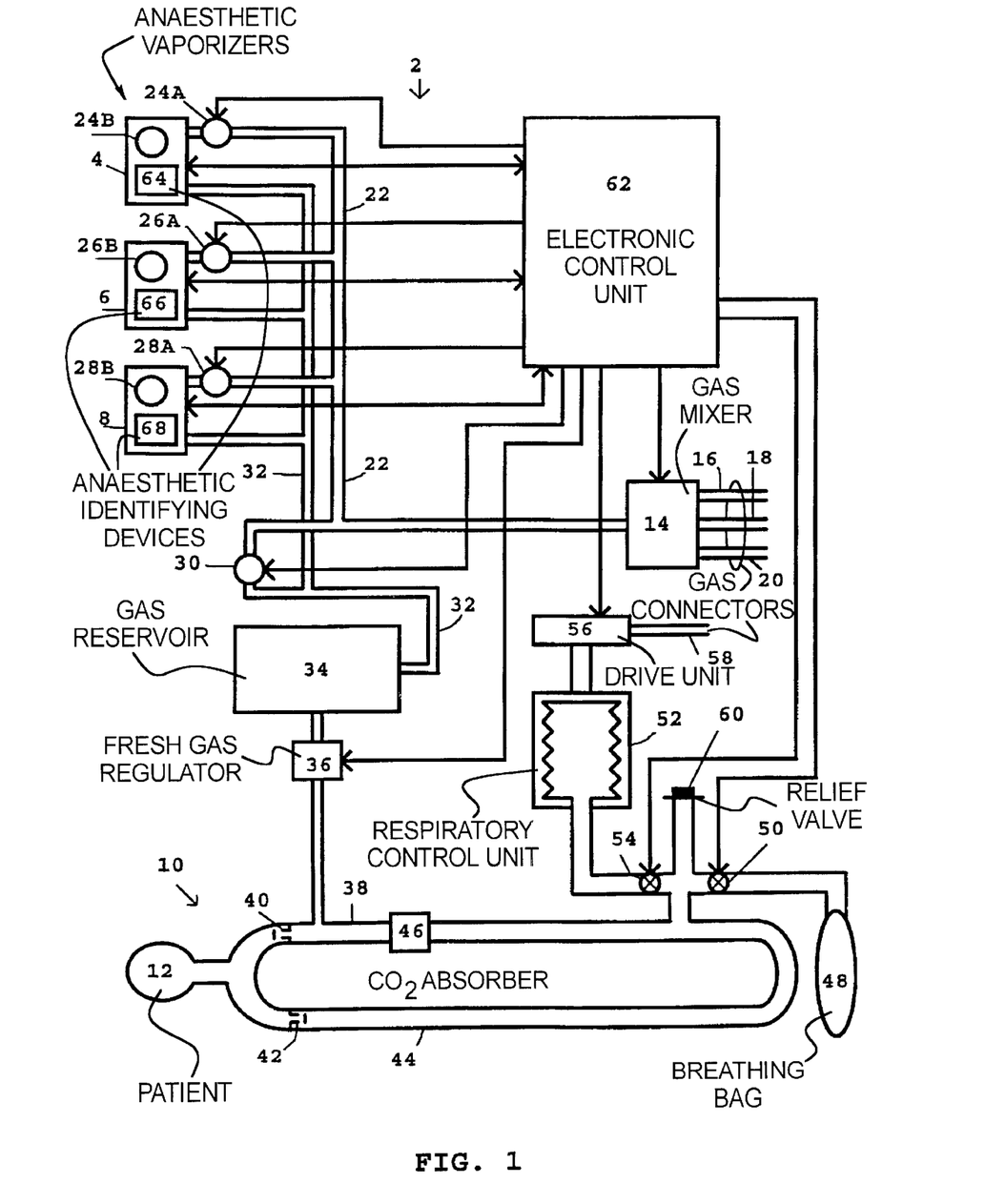
FIG. 1 is a schematic block diagram of an anaesthetic apparatus in which a device for identifying liquid anaesthetics can be used.

FIG. 1 shows an anaesthetic apparatus 2 to which a first anaesthetic vaporizer 4, a second anaesthetic vaporizer 6 and a third anaesthetic vaporizer 8 are attached for selective supply of an anaesthetic agent to a respiratory circuit 10. The respiratory circuit 10 then delivers a respiratory gas containing the anaesthetic gas to a patient 12.

The respiratory gas is fed to the anaesthetic apparatus 2 via a gas mixer 14. Gas can be carried to the gas mixer 14 via a first gas connector 16, a second gas connector 18 and a third gas connector 20. The supplied gases can be air, nitrous oxide and oxygen. If the anaesthetic apparatus 2 is only to be supplied with oxygen and nitrous oxide, the third gas connector 20 can either be turned off or also used for supplying oxygen. The supply of oxygen via two separate gas connectors 18 and 20 increases patient safety. Arriving gases are mixed in the gas mixer 14 in variable proportions to form a respiratory gas at a pre-selected pressure, whereupon a pre-selected flow of the mixed respiratory gas is carried through a first gas line 22 to the anaesthetic vaporizers 4, 6 and 8.

A first stop valve 24A is arranged by the first anaesthetic vaporizer 4. The first stop valve 24A, which is normally closed, prevents gas from the first gas line 22 from passing through the first anaesthetic vaporizer 4. When an operator activates a first setting knob 24B on the first anaesthetic vaporizer 4, the first stop valve 24A opens, and liquid anaesthetic in the first anaesthetic vaporizer 4 is vaporized so the concentration set for anaesthetic in the respiratory gas is achieved. In the corresponding manner, a second stop valve 26A is arranged by the second anaesthetic vaporizer 6, and a third stop valve 28A is arranged by the third anaesthetic vaporizer 8. The second stop valve 26A opens when a second setting knob 26B is activated, and the third stop valve 28A opens when a third setting knob at the third anaesthetic vaporizer 8 is activated. The three stop valves 24A, 26A, 28A are regulated so only one can be activated at any given time.

A fourth stop valve 30 is arranged by the first gas line 22 to allow passage of a flow of gas which has not passed through any of the anaesthetic vaporizers, 4, 6 or 8.

The anaesthetic apparatus 2 is devised so the fourth stop valve 30 Automatically opens if the first stop valve 24A, the second stop valve 26A and the third stop valve 28A are closed. This ensures that the patient has a supply of respiratory gas at all times.

Respiratory gas from the gas mixer 14 is then carried, with or without anaesthetic gas, through a second gas line 32 to a gas reservoir 34. The respiratory gas is additionally mixed in the gas reservoir 34 to ensure that vaporized anaesthetic agent is mixed with the respiratory gas to greatest possible degree before -the latter is sent on the respiratory circuit 10.

In the exemplary embodiment, the respiratory circuit 10 consists of a recirculating respiratory circuit in which the patient 12 rebreathes a greater or lesser part of the gas in the respiratory circuit 10. The mixed respiratory gas in the gas reservoir 34 thus can appropriately be designated "fresh gas" for the respiratory circuit 10. Fresh gas is supplied to the respiratory circuit 10 to compensate for the loss or leakage of gas from the respiratory circuit 10, caused by e.g. the uptake of oxygen and anaesthetic gas in the body of the patient 12 and leakage in the entire circuit system (the respiratory circuit 10 and the patient 12).

The supply of fresh gas to the respiratory circuit 10 is regulated by a fresh gas regulator 36. Fresh gas is sent to an inspiratory line 38 in the respiratory circuit 10 and delivered to the patient 12 through a first check valve 40. Gas expired by the patient 12 is carried through a second check valve 42 and an expiratory line 44. A carbon dioxide absorber 46 is also arranged in the respiratory circuit 10.

Two possible drive systems are indicated for respiratory gas in the respiratory circuit 10. The first is a manually squeezed breathing bag 48 which can be connected to the Respiratory circuit 10 via a valve 50. When the breathing bag 48 is attached to the respiratory circuit 10, a physician can manually squeeze the breathing bag 48 in order to control the inspirations and expirations of the patient 12. Alternatively, gas in the respiratory circuit 10 mechanically interact with a respiratory control unit 52, having a bag inside a container which can be connected to the respiratory circuit 10 via a valve 54. The respiratory control unit 52 is regulated by a drive unit 56, employing compressed air from a fourth gas connector 58, which can supply drive gas to the respiratory control unit 52 and can evacuate drive gas therefrom. Surplus gas in the respiratory circuit 10 is evacuated via a relief valve 60.

The anaesthetic apparatus 2 is controlled and monitored by a control device 62. The control device 62 regulates the operation of the gas mixer 14, drive unit 56, fresh gas regulator 36, stop valves 24A, 26A, 28A and 30 and anaesthetic vaporizers 4, 6 and 8. The control device 62 also receives information about settings for functions, such as breathing rate, desired tidal volume, respiratory gas composition etc., made by staff. Other functions and tasks performed by the control device 56 will be apparent from the following.

In order e.g., to identify the anaesthetic agents connected to the anaesthetic apparatus 2, each anaesthetic vaporizer 4, 6 and 8 includes a device 64, 66 or 68 for identifying the anaesthetic agent in the respective anaesthetic vaporizer 4, 6 or 8. Information ascertained therein about the anaesthetic agent in each anaesthetic vaporizer 4, 6 and 8 is sent to the control device 62.

A number of embodiments of the devices 64, 66 and 68 are possible. Eleven embodiments of the device 64, 66 and 68 are described below.

Figure 2:
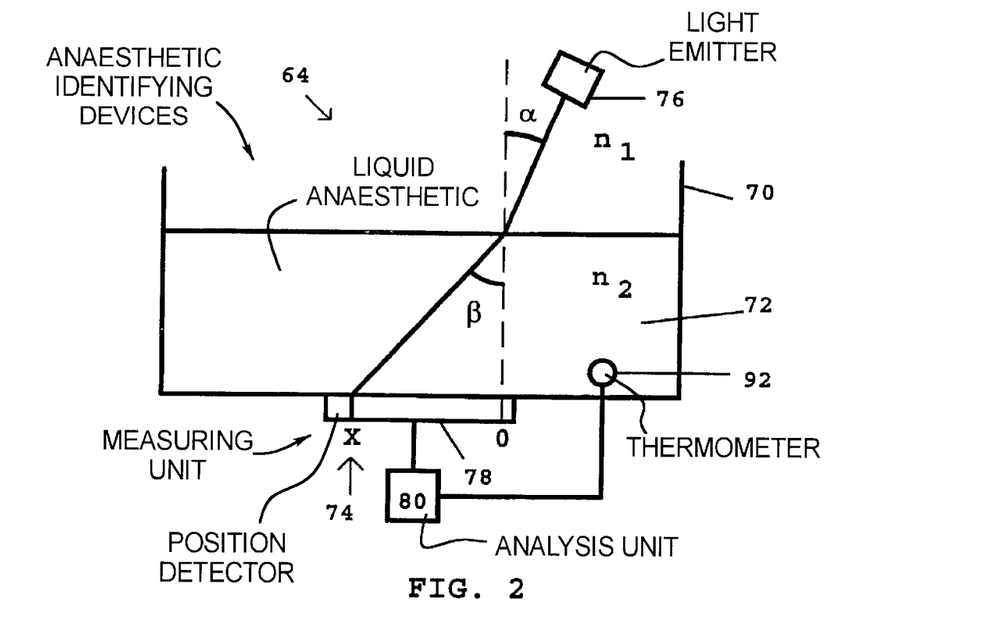
FIG. 2 shows a first embodiment of a device according to the invention for identifying liquid anaesthetics.

FIG. 2 shows a first embodiment of the device 64 (the designations 66 and 68 will henceforth be omitted for simplicity) according to the present invention. The device 64 can, but does not need to, include a container 70 for holding a liquid anaesthetic 72. The device 64 also has a measuring unit 74 and an analysis unit 80. The measuring unit 74 includes a light-emitter 76 and a position detector 78. The light-emitter 76 emits a light beam which strikes the surface of the liquid anaesthetic 72 at a specific angle of incidence $\alpha$. Since the anaesthetic agent 72 has a refractive index $n_2$ which differs from the refractive index $n_1$ of the medium (e.g. air) above the anaesthetic agent 72, the light beam is refracted or deflected in the liquid at an angle of refraction $\beta$. The degree to which the light is refracted depends on the refractive index $n_2$ of the liquid anaesthetic. This relationship can be expressed with Beer's law of refraction which states that:

$$n_1 \sin \alpha = n_2 \sin \beta$$

The deflected light beam strikes the position detector 78 at x. If $n_1$, $\alpha$, the level of liquid in the container 70 and the temperature of the liquid are known, the refractive index $n_2$ of the liquid anaesthetic 72 can be determined from x.

Temperature is measured by a thermometer 92, which is connected to the analysis unit 80 for providing a measurement of the temperature thereto.

The level can also be measured (not shown) but the container 70 could be constructed so that a defined level of liquid is maintained in the measurement (analysis) area.

The analysis unit 80, connected to the position detector 72 and the thermometer 92 performs this determination of $n_2$ which is used for establishing the liquid anaesthetic's identity. The position detector 78 can also be equipped with a measuring rod (not shown) which is marked for directly indicating the identity of the anaesthetic agent 72 at the position the light beam strikes the position detector 78. (In the latter case, a control of the temperature and level of the liquid to pre-selected constants is necessary.)

In another version, a ruler can serve as the position detector 78, and a window is arranged so the ruler can be observed. A light spot will be seen when the light beam strikes the ruler, and the identity of the anaesthetic agent can be read on the ruler (which accordingly serves as an analysis unit).

The analysis unit 80 is also capable of determining whether a mixture of at least two anaesthetic liquids is present. Basically, the light beam will then illuminate a position on the rod 78 which should not be lit.

It should be noted that numerous variations of this arrangement are possible. For instance, the light source 76 can be immersed in the liquid and the rod 78 placed above the surface. A liquid—glass interface can be used instead of a liquid—air interface. The container 70 can have a prismatic shape, and the light can be transmitted through the prism for determining the deflection (refractive index of the liquid). The rod 78 can be made to fluoresce where the transmitted light hits it, thereby illuminating the spot of interest.

Figure 3:
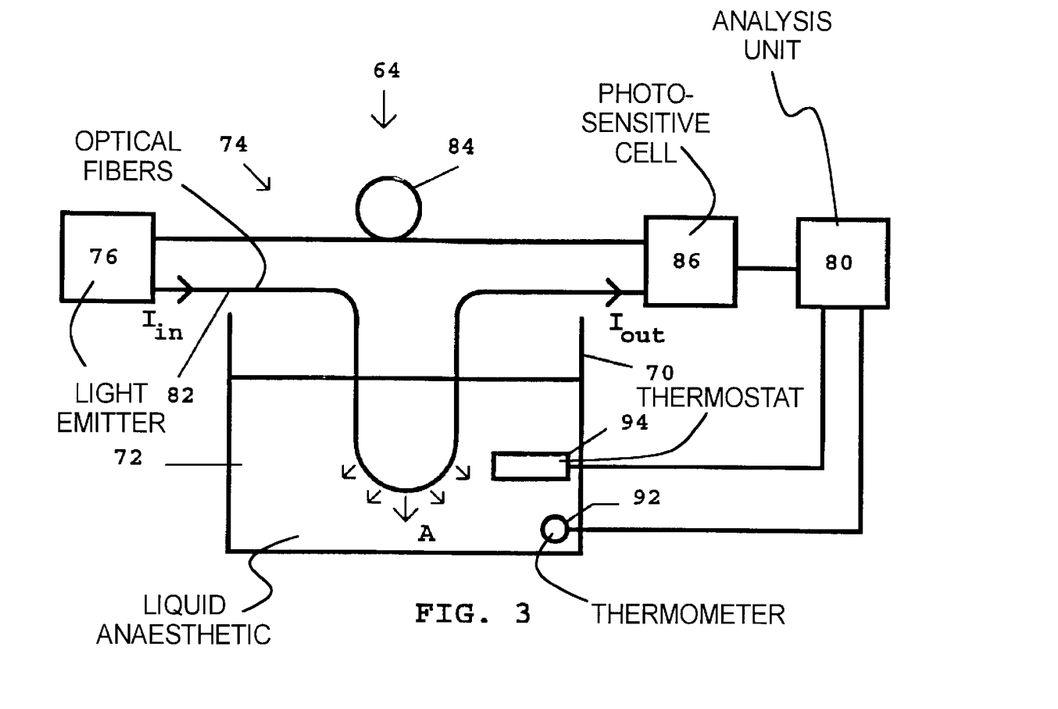
FIG. 3 shows a second embodiment of a device according to the invention for identifying liquid anaesthetics.

FIG. 3 shows a second embodiment of the device 64 according to the present invention. The device 64 has a container 70 (which does not need to be included in the device 64) for holding an anaesthetic agent 72 in liquid form. The device 64 also has a measuring unit 74, a thermometer 92 and an analysis unit 80. In the alternative, a thermostat 94 can be used for controlling the temperature of the liquid maintaining it at a selected level. Such control could be exercised from the analysis unit 80.

The measuring unit 74 has a light-emitter 76, a first optical fiber 82, a second optical fiber 84 and a photosensitive cell 86. The analysis unit 80 is connected to the photosensitive cell 86 and to the thermometer 92. The first optical fiber 82 has a first end coupled the light-emitter 76 for receiving light ($I_{in}$) and an opposite end coupled to the photosensitive cell 86 for emitting transmitted light ($I_{out}$). The first optical fiber 82 is also partially immersed in the liquid anaesthetic 72.

The immersed part has at least one curved section. In the illustrated device 64, the immersed part of the first optical fiber 82 also has two substantially parallel sections. In particular, the parallel sections should pass through the liquid surface at a right angle in order to avoid unwanted leakage of light.

The second optical fiber 84 has the same length as the first optical fiber 82 and has a first end arranged by the light-emitter 76 and its other end arranged by the photosensitive cell 86. The second optical fiber 84 is intended to supply a reference value. When an optical fiber is curved, as the first optical fiber 82 is, light leaks out of the curved section, as designated with the arrows A. No light leaks out of the optical fiber's straight sections. The amount of light leaking out of the curved section depends on the refractive index of the liquid anaesthetic 72, in addition to the fiber's radius of curvature and diameter (however, these latter valves are known and taken into consideration in the algorithms for determining the identity of the liquid anaesthetic 72). The refractive index can therefore be determined based on the $I_{in}/I_{out}$ ratio.

The measuring unit 74 is thus devised to determine the amount of light leaking out of the curved section of the first optical fiber 82 as the parameter related to refractive index. Since the anaesthetic agent is unknown, the measuring unit 80 will, with the aid of this parameter (amount of leaked light A) and the reference value, identify the anaesthetic agent, since the amount of light received in relation to the amount emitted is a measure of the refractive index of the liquid. All other parameters (e.g.,temperature) are known.

Here as well, numerous variations are possible. Some will be described below, others can be conceived. For instance, the curved part of the fiber 82 can have a number of different shapes for refining the measurement to the prevailing conditions, i.e., the interval of refractive indices (anaesthetic agents), the material of the fiber, the frequency or frequencies of light that is used, etc.

Figure 4:
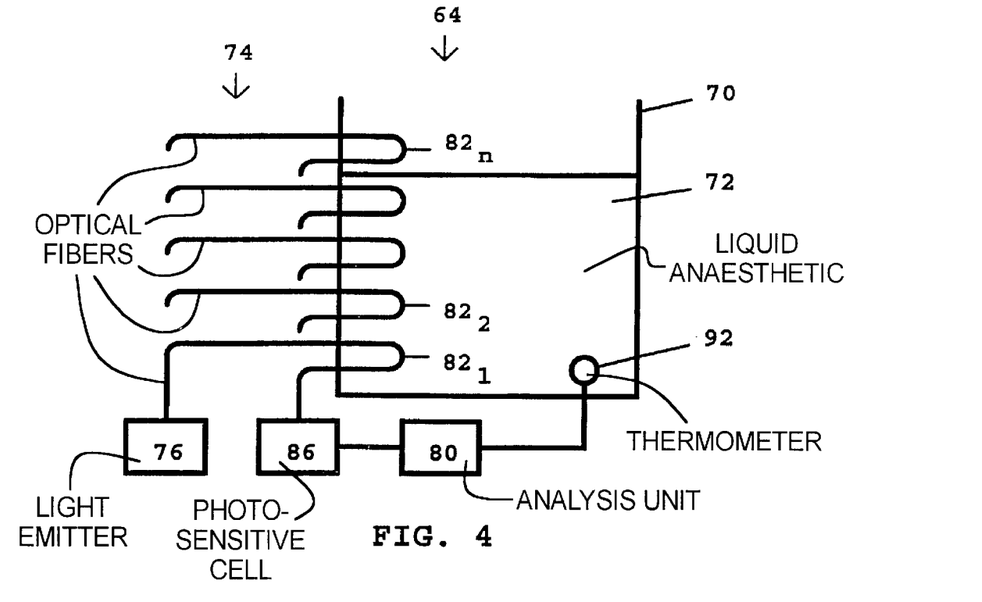
FIG. 4 shows a third embodiment of a device according to the invention for identifying liquid anaesthetics.

FIG. 4 shows a third embodiment of the device 64 according to the present invention. The device 64 has a container 70 (which does not need to be included in the device 64) for holding an anaesthetic agent 72 in liquid form. The device 64 also has a measuring unit 74, a thermometer 92 and an analysis unit 80. As in the above embodiment, the thermometer 92 can be replaced with a thermostat for maintaining a pre-selected temperature of the liquid anaesthetic. The measuring unit 74 includes a light-emitter 76, n optical fibers $82_1$, $82_2$, . . . , $82_n$ and a photosensitive cell 86. Each optical fiber has a first end arranged by the light-emitter 76 and an opposite end arranged by the photosensitive cell 86. Each of the fibers $82_1$, $82_2$, . . . , $82_n$ has a curved section, and the fibers are arranged so their curved sections are respectively arrayed at different levels in the container 70.

Since the amount of light leaking out of the curved section of the optical fiber depends on the refractive index of the medium, the device 64 can determine whether a specific fiber's curved section is in the liquid anaesthetic 72. The number of fibers arranged in the liquid anaesthetic 72 designates the level of the liquid in discrete steps. The greater the number of fibers $82_1$, $82_2$, . . . , $82_n$ used, the greater the accuracy in determination of the level of the liquid. One advantage of this embodiment is that the identity of the anaesthetic agent can be determined at the same time as the level of the liquid. Also, if there is a heterogeneous mixture of two anaesthetics, this can be detected by the device since the refractive index will vary at different levels (i.e.,different fibers $82_i$ will measure different refractive indices). One light-emitter and one photosensitive cell can obviously be utilized for each fiber.

Figure 5:
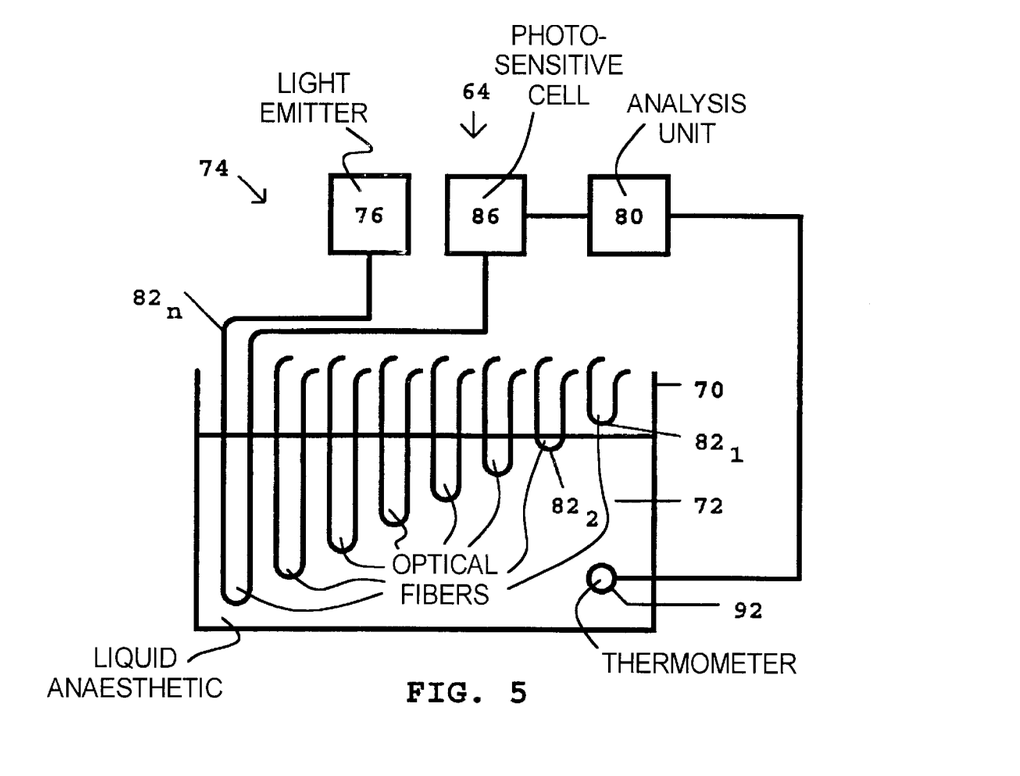
FIG. 5 shows a fourth embodiment of a device according to the invention for identifying liquid anaesthetics.

FIG. 5 shows a fourth embodiment of the device 64 according to the present invention. The device 64 has a container 70 (which does need to be included in the device 64) for holding an anaesthetic agent 72 in liquid form. The device 64 also has a measuring unit 74, a thermometer 92 and an analysis unit 80. As in the above embodiments, the thermometer 92 can be replaced with a thermostat for maintaining a pre-selected temperature of the liquid anaesthetic. The measuring unit 74 includes a light-emitter 76, n optical fibers $82_1$, $82_2$, . . . , $82_n$ and a photosensitive cell 86. Each optical fiber $82_1$, $82_2$, . . . , $82_n$ has a first end arranged by the light-emitter 76 and its other end arranged by the photosensitive cell 86. All the fibers $82_1$, $82_2$, . . . , $82_n$ has a curved section, and the fibers $82_1$, $82_2$, . . . , $82_n$ are arranged so they respectively descend into the container 70 to differing degrees, i.e. they are arranged at different levels. This embodiment is also based on the fact that the amount of light leaking out of the curved section of an optical fiber depends on the refractive index of the medium surrounding the curved section. The number of fibers arranged in the liquid anaesthetic 72 designate the level of the liquid in discrete steps. As in the previous embodiment, a identity of the anaesthetic agent can be determined at the same time as the determination of the level of the liquid. Likewise, a determination of the presence of a mixture can be made simultaneously. A number of light-emitters and a number of photosensitive cells can also be provided in this embodiment.

Figure 6:
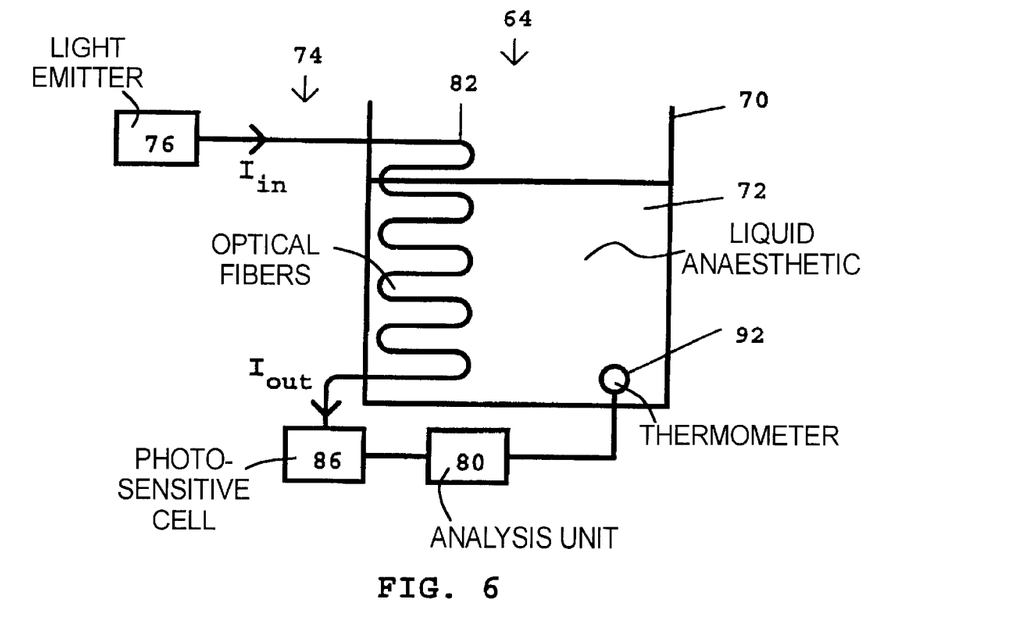
FIG. 6 shows a fifth embodiment of a device according to the invention for identifying liquid anaesthetics.

FIG. 6 shows a fifth embodiment of the device 64 according to the present invention. The device 64 has a container 70 (which does not need to be included in the device 64) for holding an anaesthetic agent 72 in liquid form. The device 64 also has a measuring unit 74, a thermometer 92 and an analysis unit 80. As in the above embodiments the thermometer 92 can be replaced with a thermostat for maintaining a constant temperature. The measuring unit 74 includes a light-emitter 76, an optical fiber 82 and a photosensitive cell 86. The optical fiber 82 has a first end arranged by the light-emitter 76 and an opposite end by the photosensitive cell 86. The optical fiber 82 has a number of curved sections arranged at different levels in the container 70. The straight sections of the fiber 82 are substantially parallel to the level of any liquid which is present. This embodiment is also based on the fact that the amount of light leaking out of the curved section of an optical fiber depends on the refractive index of the medium around the curved section. In this case, the identity of the anaesthetic agent and the level of the liquid can be determined simultaneously in discrete steps. The requirements for doing so is that the initial conditions are known, i.e., that the container 70 is filled to a specific level with the liquid anaesthetic. Before allowing any part of the liquid to be vaporized, the identity of the anaesthetic agent is determined. This determination can be made from the $I_{in}/I_{out}$ ratio. After determination of the identity of the anaesthetic agent (or determination of a mixture) liquid may be used for narcosis. As the level drops, the leakage of light changes. This is determined by the analysis unit 80 and the current level can be calculated.

Figure 7:
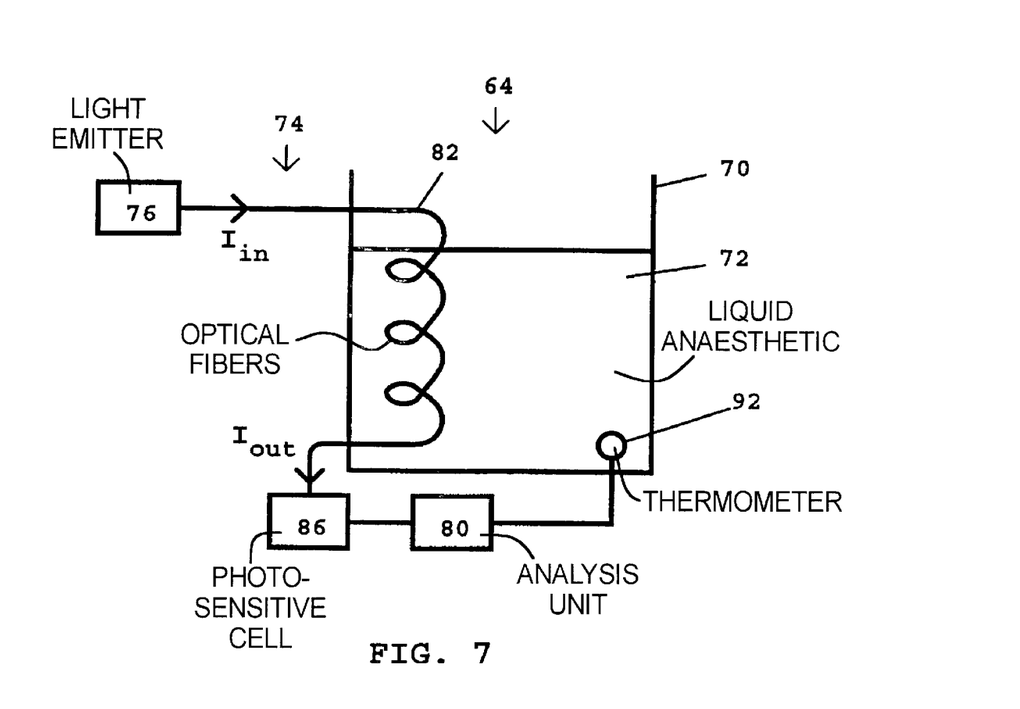
FIG. 7 shows a sixth embodiment of a device according to the invention for identifying liquid anaesthetics.

FIG. 7 shows a sixth embodiment of the device 64 according to the present intention. The device 64 has a container 70 (which does no need to be included in the device 64) for holding an anaesthetic agent 72 in liquid form. The device 64 also has a measuring unit 74, a thermometer 92 and an analysis unit 80. As in the above embodiments, the thermometer 92 can be replaced with a thermostat for maintaining the temperature of the liquid constant. The measuring unit 74 includes a light-emitter 76, an optical fiber 82 and a photosensitive cell 86. The optical fiber 82 has a first end arranged by the light-emitter 76 and an opposite end arranged by the photosensitive cell 86. The optical fiber has the shape of a coil arranged in the container 70 so the coil's axial center line is perpendicular to the level of any liquid which is present. The signal $l_{out}$ measured by the photosensitive cell 86 is a function of the level of liquid in the container 70. Since a coil primarily consists of curved sections, light leaks out of the entire coil. In this case also, the identity of the anaesthetic agent and the level of the liquid can be determined simultaneously in discrete steps. The requirement for doing so is that the initial conditions are known, i.e., that the container 70 is filled up to a specific level with the liquid anaesthetic. Before allowing any part of the liquid to be vaporized, the identity of the anaesthetic agent is determined. This can be made from the $I_{in}/I_{out}$ ratio. After determination of the identity of the anaesthetic agent (or determination of a mixture) liquid may be used for narcosis. As the level drops, the leakage of light changes. This is determined by the analysis unit and the current level can be calculated.

Figure 8:
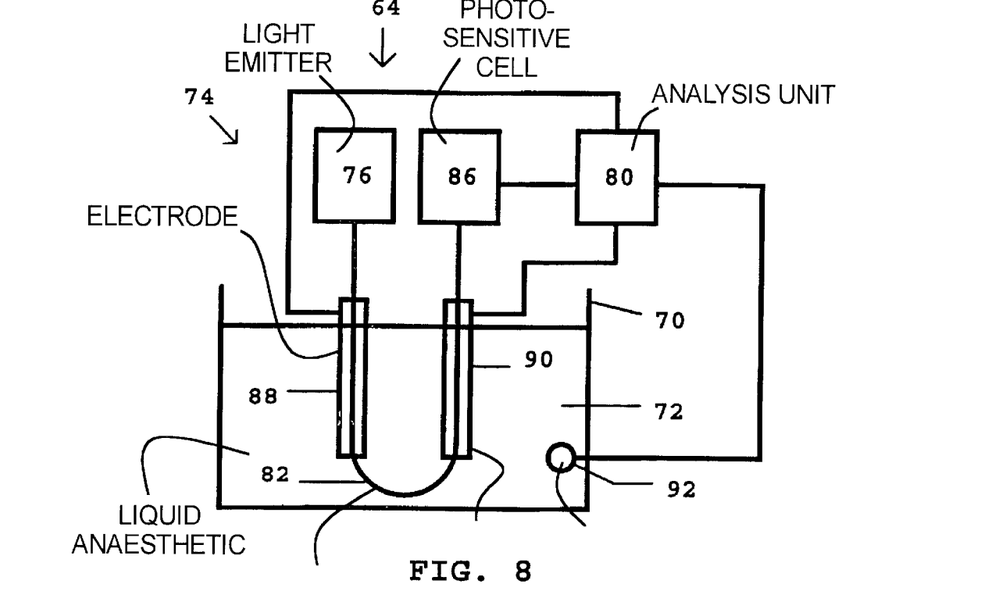
FIG. 8 shows a seventh embodiment of a device according to the invention for identifying liquid anaesthetics.

FIG. 8 shows a seventh embodiment of the device 64 according to the present invention. The device 64 has a container 70 (which does no need to be included in the device 64) for holding an anaesthetic agent 72 in liquid form. The device 64 also has a measuring unit 74, a thermometer 92 and an analysis unit 80. The thermometer can be replaced with a thermostat for maintaining a constant temperature in the liquid. The measuring unit 74 includes a light-emitter 76, an optical fiber 82, a photosensitive cell 86, a first electrode 88 and a second electrode unit 90. The optical fiber 82 has a first end arranged by the light-emitter 76 and an opposite end arranged by the photosensitive cell 86. The optical fiber 82 also has a curved section arranged in the container 70. The photosensitive cell 86 and the two electrodes 88 and 90 are connected to the analysis unit 80. The two electrodes 88, and 90 are arranged along the straight sections of the optical fiber and are arrayed in the container 70 so they come into contact with the liquid anaesthetic 72 when the latter exceeds a specific level in the container 70. The optical fiber 82 is used in the same way as the embodiment according to FIG. 3, i.e., for determining the identity or temperature of the anaesthetic agent 72. With knowledge thereof, the dielectric constant $\in_r$ of the liquid can be obtained. The electrodes 88 and 90 can be used for measuring the capacitance C of the liquid between the electrodes 88, and 90. Since the capacitance C of the liquid varies with the level of the liquid, the analysis unit 80 can determine the level of the liquid from the capacitance C established for the identified liquid.

Figure 9:
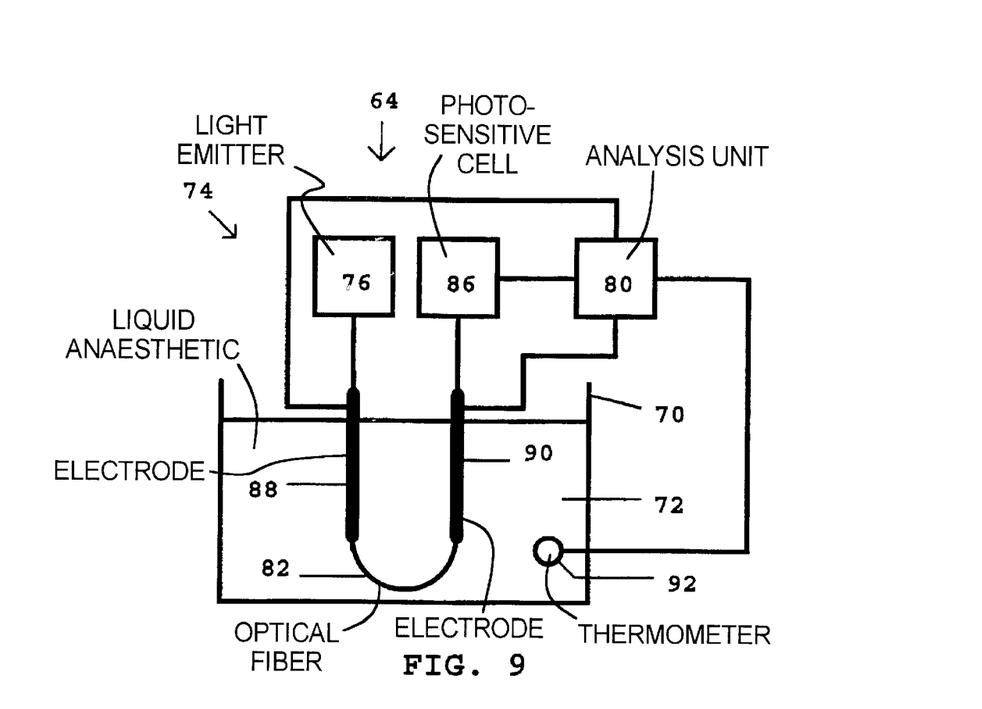
FIG. 9 shows an eighth embodiment of a device according to the invention for identifying liquid anaesthetics.

FIG. 9 shows an eighth embodiment of the device 64 according to the present invention. Identical parts to those in FIGS. 8 and 9 have been assigned the same reference designations. The difference compared to the device 64 according to FIG. 8 is that the two electrodes 88 and 90 are formed by respective metallized surface areas on the straight, parallel sections of the optical fiber 82. Otherwise, the device of FIG. 9 operates the same as the device 64 according to FIG. 8.

Figure 10:
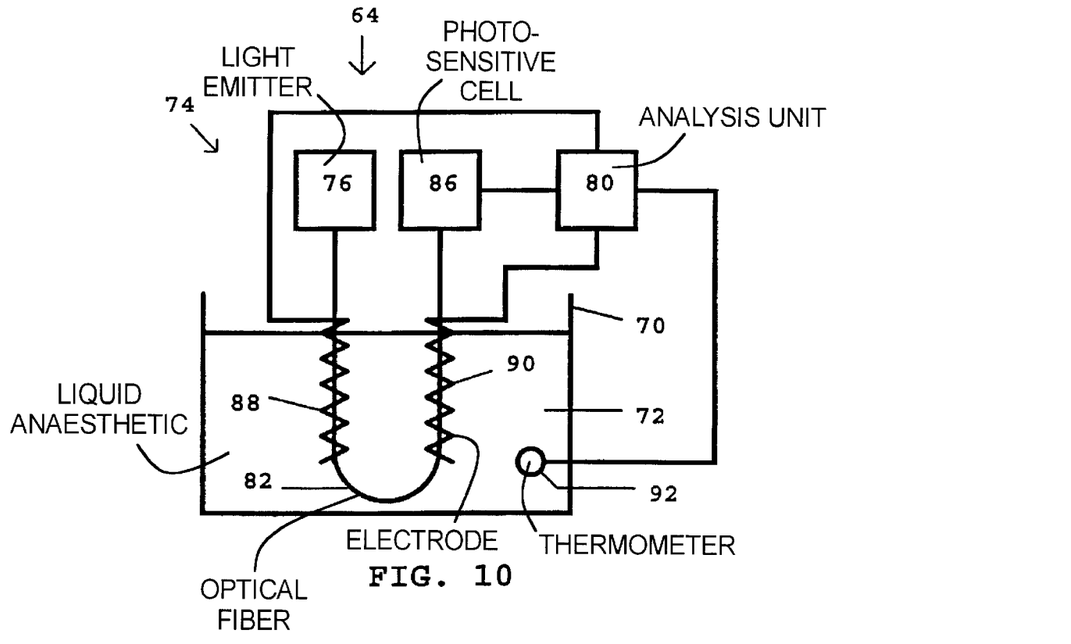
FIG. 10 shows a ninth embodiment of a device according to the invention for identifying liquid anaesthetics.

FIG. 10 shows a ninth embodiment of the device 64 according to the present invention. Identical parts to those in FIGS. 8–10 have been assigned the same reference designations. The difference compared to the devices 64 according to FIGS. 8 and 9 is that in the device of FIG. 10, the two electrodes 88 and 90 are formed by metal wire wound around the straight, parallel sections of the optical fiber 82. Otherwise, the device of FIG. 10 operates the same as the devices 64 according to FIGS. 8 and 9.

Figure 11:
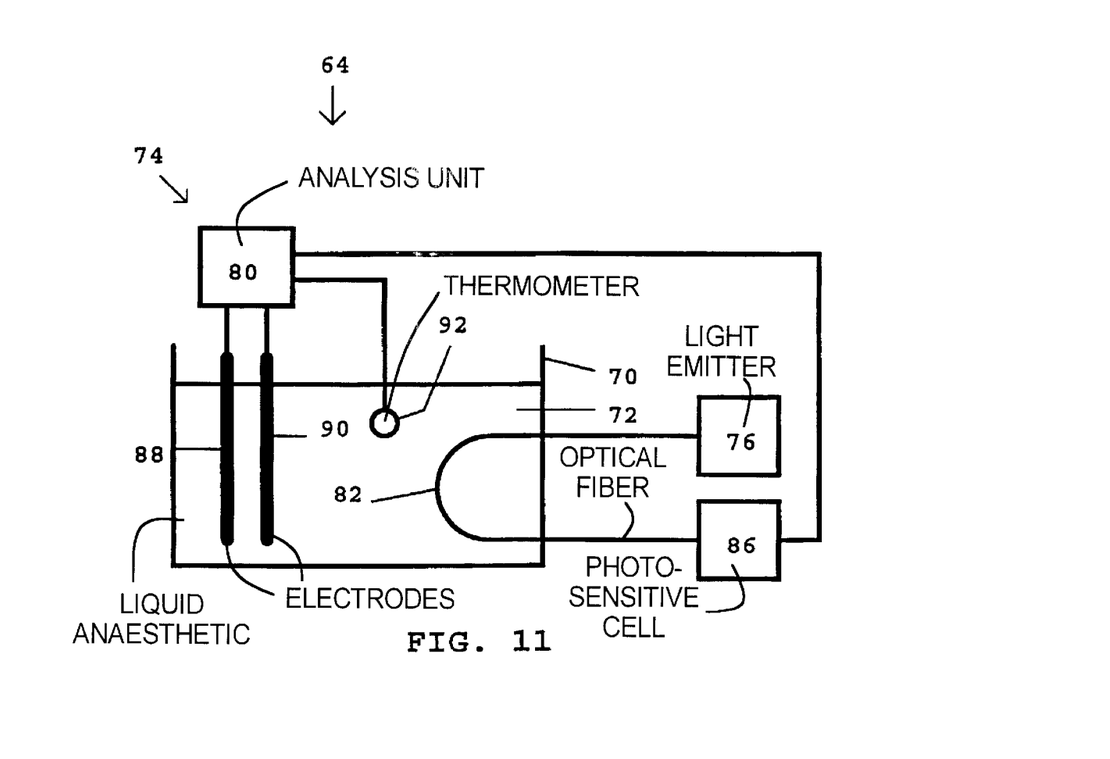
FIG. 11 shows a tenth embodiment of a device according to the invention for identifying liquid anaesthetics.

FIG. 11 shows a tenth embodiment of the device 64 according to the present invention. Identical parts to those in FIGS. 8–11 have been assigned the same reference designations. The difference compared to the devices 64 according to FIGS. 8–10 is that in the device of FIG. 10, the two electrodes 88 and 90 are physically separate from the optical fiber 82. The two electrodes 88 and 90 and the optical fiber 82 do not need to arrayed in the illustrated manner according to FIG. 11. Otherwise, the device of FIG. 11 operates the same as the devices 64 according to FIGS. 8–10.

Figure 12:
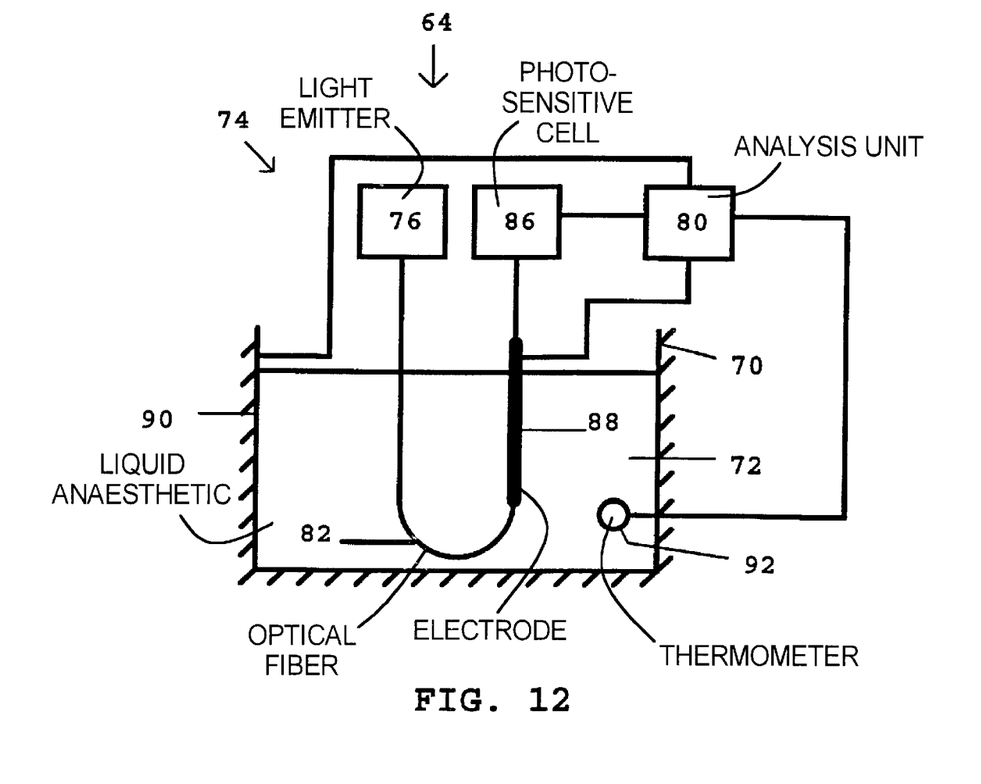
FIG. 12 shows an eleventh embodiment of a device according to the invention for identifying liquid anaesthetics.

FIG. 12 shows an eleventh embodiment of the device 64 according to the present invention. Identical parts to those in FIGS. 8–12 have been assigned the same reference designations. The different aspect of this embodiment is that the first electrode 88 is formed by a metallic deposit on the optical fiber 82, and the second electrode 90 is formed by a metallic deposit on the interior of the container 70 for the liquid anaesthetic 72. Otherwise, the device of FIG. 12 operates the same as the devices 64 according to FIGS. 8–11, i.e. the optical fiber 82 is used for determining the identity or temperature of the liquid anaesthetic 72, and the level of liquid is measured by the varying capacitance C between the two electrodes 88 and 90.

The analysis unit 80 in the illustrated devices 64 for measuring the level of liquid can also be equipped with means for issuing an alarm indication, e.g., in the form of an acoustic or visual signal, when a mixture of anaesthetic agents is determined, when the set concentration is outside the normal range for the identified anaesthetic (i.e., there is a risk that the vaporizer is completely filled with wrong anaesthetic or that the anaesthesiologist has mistakenly activated the wrong vaporizer), and/or when the liquid drops below a specific, pre-defined level in the container 70.

The optical fiber 82 can be made of e.g. fiberglas. Different cladding can used along the fiber 82 for reducing any unnecessary losses of light. It would be sufficient to have only the immersed part exposed (unclad) for leakage and the rest of the fiber 82 enclosed for guaranteeing reflection of the light in the fiber 82.

The light-emitter 76 can e.g., be a light-emitting diode, a laser, a lamp or any other light generator. The photosensitive cell 86 can e.g., be a photodiode, photoresistor, or other light detector.

The invention is not limited to the illustrated embodiments. A number of variations are possible within the scope of the invention. For example, combinations of the disclosed embodiments can be made were appropriate.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for use with an anaesthetic administration apparatus for identifying at least one liquid anaesthetic in said anaesthetic administration apparatus, said device comprising:

means for determining at least one parameter related to a refractive index of a liquid anaesthetic to be identified;

means for determining a temperature of said liquid anaesthetic to be identified; and analysis means for identifying said liquid anaesthetic to be identified from said at least one parameter at said temperature.

2. A device as claimed in claim 1 wherein said analysis means comprises means for determining, from said at least one parameter at said temperature, whether said liquid anaesthetic to be identified comprises a mixture of at least two liquid anaesthetics.

3. A device as claimed in claim 2 wherein said mixture comprises two liquid anaesthetics and said analysis unit comprises means for identifying an identity of each of said two liquid anaesthetics comprising said mixture, and a composition of each of said two liquid anaesthetics in said mixture.

4. A device as claimed in claim 1 wherein said means for determining a temperature of said liquid anaesthetic to be identified comprises a thermometer.

5. A device as claimed in claim 1 wherein said means for determining a temperature of the liquid anaesthetic to be identified comprises a thermostat which maintains said liquid anaesthetic to be identified at a predetermined temperature.

6. A device as claimed in claim 1 wherein said measuring means comprises a light-emitter which emits a light beam striking a surface of said liquid anaesthetic to be identified at a known angle of incidence, and a position detector on which said light beam is incident after striking said surface which indicates a deflection of said light beam in said liquid anaesthetic, said deflection comprising said at least one parameter related to the refractive index of said liquid anaesthetic to be identified and being dependent on the refractive index of said liquid anaesthetic to be identified and a level of said liquid anaesthetic to be identified.

7. A device as claimed in claim 6 wherein said position detector comprises a measuring rod for indicating the identity of said liquid anaesthetic to be identified dependent on a position at which said light beam strikes said measuring rod.

8. A device as claimed in claim 1 wherein said measuring means comprises a light-emitter and a photosensitive cell and at least one optical fiber extending between said light-emitter and said photosensitive cell, said optical fiber having a curved section immersed in said liquid anaesthetic to be identified, and wherein said photosensitive cell measures an amount of light leaking out of said curved section of said optical fiber as said at least one parameter related to refraction.

9. A device as claimed in claim 8 wherein said at least one optical fiber comprises a first optical fiber, and wherein said measuring means comprises a second optical fiber, not immersed in said liquid anaesthetic to be identified, having a length identical to a length of said first optical fiber, said second optical fiber supplying a reference value and said analysis unit being supplied with said reference value and with said parameter related to refraction for identifying at least one of the identity of said liquid anaesthetic to be identified, the temperature of said liquid anaesthetic to be identified, and a level of said liquid anaesthetic to be identified, from said parameter related to refractive index and said reference value.

10. A device as claimed in claim 8 comprising a plurality of optical fibers connectable to said light-emitter, and disposed at respectively different levels in said liquid anaesthetic to be identified, for determining a level of said liquid anaesthetic to be identified in discrete steps.

11. A device as claimed in claim 8 wherein said at least one optical fiber has a plurality of curved sections respectively disposed at different levels in said liquid anaesthetic to be identified for identifying a level of said liquid anaesthetic to be identified.

12. A device as claimed in claim 8 wherein said analysis means comprises means for generating an alarm if said level of said liquid anaesthetic to be identified falls below said curved section of said optical fiber.

13. A device as claimed in claim 8 further comprising two electrodes in contact with said liquid anaesthetic to be identified, and wherein said analysis means comprises means for measuring a capacitance of said liquid anaesthetic to be identified between said electrodes as a measure of a level of said liquid anaesthetic to be identified.

14. A device as claimed in claim 13 wherein said curved section of said optical fiber immersed in said liquid anaesthetic to be identified comprises two substantially parallel sections, and wherein said electrodes are respectively disposed on said substantially parallel sections.

15. A device as claimed in claim 14 wherein each of said electrodes comprises a metallized surface area on a respective parallel section of said optical fiber.

16. A device as claimed in claim 14 wherein each of said electrodes comprises a metal wire wound around a respective parallel section of said optical fiber.

17. A device as claimed in claim 14 further comprising a container containing said liquid anaesthetic to be identified, and wherein said electrodes comprise first and second electrodes, said first electrode comprising a metallized surface area on said optical fiber, and said second electrode comprising a metal deposit on an interior of said container.

* * * * *